(12) United States Patent
Shaw

(10) Patent No.: US 10,759,143 B2
(45) Date of Patent: Sep. 1, 2020

(54) PROTECTIVE ARTICLES

(71) Applicant: Gant Innovations Limited, Leicester (GB)

(72) Inventor: Gail Shaw, Leicester (GB)

(73) Assignee: Gant Innovations Limited, Leicester (GB)

(*) Notice: Subject to any disclaimer, the term of this patent is extended or adjusted under 35 U.S.C. 154(b) by 0 days.

(21) Appl. No.: 15/537,982

(22) PCT Filed: May 14, 2015

(86) PCT No.: PCT/EP2015/060734
§ 371 (c)(1),
(2) Date: Jun. 20, 2017

(87) PCT Pub. No.: WO2016/102080
PCT Pub. Date: Jun. 30, 2016

(65) Prior Publication Data
US 2017/0341338 A1 Nov. 30, 2017

(30) Foreign Application Priority Data

Dec. 22, 2014 (GB) .................................. 1422969.4
Mar. 24, 2015 (GB) .................................. 1504973.7

(51) Int. Cl.
*B32B 7/06* (2019.01)
*A47G 11/00* (2006.01)
(Continued)

(52) U.S. Cl.
CPC ............... *B32B 7/06* (2013.01); *A41B 13/10* (2013.01); *A41D 13/04* (2013.01); *A47C 31/00* (2013.01); *A47G 11/002* (2013.01); *A47G 11/003* (2013.01); *A47G 23/03* (2013.01); *A47G 23/0303* (2013.01); *A61B 46/20* (2016.02); *B31D 1/021* (2013.01); *B31D 1/04* (2013.01);
(Continued)

(58) Field of Classification Search
CPC .... A47G 11/002; A47G 11/003; A47G 23/03; A47G 23/0303; B31D 1/04; B32B 7/06; B32B 7/12; B32B 27/08; B32B 15/082; A47C 31/00; A41D 13/04; A41B 13/10; B60J 11/08; A61B 2046/205; A61B 46/20; Y10T 428/14
See application file for complete search history.

(56) References Cited

U.S. PATENT DOCUMENTS 4,306,316 A * 12/1981 Klepfer ................. A41B 13/10
2/48
4,690,679 A 9/1987 Mattingly, III et al.
(Continued)

FOREIGN PATENT DOCUMENTS

BE 1015658 A3 7/2005
DE 20306817 U1 9/2003
(Continued)

*Primary Examiner* — Patricia L. Nordmeyer
(74) *Attorney, Agent, or Firm* — The Webb Law Firm

(57) ABSTRACT

A protective article is disclosed including a sheet with a first surface, and at least one adhesive portion arranged on the first surface. The adhesive is a water-based adhesive, such as a water-based acrylic adhesive, that allows the sheet to be non-permanently adhered to an object. The adhesive may be sprayed, rolled, printed, or stamped onto the first surface.

19 Claims, 4 Drawing Sheets

(51) Int. Cl.

| | | |
|---|---|---|
| *A47G 23/03* | (2006.01) | |
| *B31D 1/04* | (2006.01) | |
| *A41B 13/10* | (2006.01) | |
| *B31D 1/02* | (2006.01) | |
| *A61B 46/20* | (2016.01) | |
| *A41D 13/04* | (2006.01) | |
| *A47C 31/00* | (2006.01) | |
| *B32B 7/12* | (2006.01) | |
| *B32B 15/082* | (2006.01) | |
| *B32B 27/08* | (2006.01) | |
| *B60J 11/08* | (2006.01) | |

(52) U.S. Cl.
CPC .............. *B32B 7/12* (2013.01); *B32B 15/082* (2013.01); *B32B 27/08* (2013.01); *B60J 11/08* (2013.01); *A61B 2046/205* (2016.02)

(56) References Cited

U.S. PATENT DOCUMENTS

| | | | | |
|---|---|---|---|---|
| 5,194,299 A | * | 3/1993 | Fry | C09J 7/38 427/208.6 |
| 5,262,462 A | * | 11/1993 | Watanabe | C08F 8/00 524/284 |
| 5,277,954 A | * | 1/1994 | Carpenter | A61F 13/041 428/71 |
| 5,670,226 A | * | 9/1997 | Yoshizawa | B32B 7/06 428/40.1 |
| 6,281,298 B1 | | 8/2001 | Papsin, Jr. | |
| 2005/0158567 A1 | | 7/2005 | Carper et al. | |
| 2007/0185469 A1 | | 8/2007 | Green | |
| 2012/0189827 A1 | | 7/2012 | Shaw | |

FOREIGN PATENT DOCUMENTS

| | | |
|---|---|---|
| DE | 202004017373 U1 | 3/2005 |
| EP | 0471587 A1 | 2/1992 |
| EP | 0848923 A1 | 6/1998 |
| FR | 2763496 A1 | 11/1998 |
| FR | 2787002 A3 | 6/2000 |
| WO | 9426834 A1 | 11/1994 |
| WO | 0235975 A1 | 5/2002 |
| WO | 2011039533 A1 | 4/2011 |

* cited by examiner

PROTECTIVE ARTICLES

CROSS-REFERENCE TO RELATED APPLICATIONS

This application is the United States national phase of International Application No. PCT/EP2015/060734 filed May 14, 2015, and claims priority to United Kingdom Patent Application Nos. 1422969.4 and 1504973.7, filed Dec. 22, 2014, and Mar. 24, 2015, respectively, the disclosures of which are hereby incorporated in their entirety by reference.

BACKGROUND OF THE INVENTION

Field of the Invention

The present invention relates to protective articles for protecting objects or parts thereof from damage and/or being tarnished. More specifically, the invention relates to protective articles configured to be removably adhered to an object being protected.

The invention also relates to methods of manufacture of and apparatus for the manufacture of such protective articles.

Description of Related Art

There are many situations where a protective article may be conveniently used to protect a more expensive object, e.g. from spills or dirt. For instance, a bib or a napkin may be used to protect a diner's clothes. In other cases, an object such as a piece of furniture may need to be protected, as in the case of a table cloth or a place mat.

Generally, this protection may be achieved by placing a sheet, typically of paper or cloth, across or over the object to be protected, for example placing a napkin across the lap, or a table cloth across a table. However, these sheets of material are liable to slip or fall off, leaving parts of the object exposed. In other circumstances, the protective garment may have to be tied to the object, as is the case of a bib. This can be particularly difficult for people with reduced mobility or dexterity.

In the case of napkins, it may be inconvenient and/or difficult for a person to pick up and replace a napkin that has fallen off his/her lap. This may be especially so if, for example, the person is eating outside and a breeze is blowing, or is in a restricted space such as on board a train, bus, boat or aeroplane, or the person has restricted mobility or dexterity, e.g. due to illness or injury.

To give another example, when sitting eating a meal people typically place a napkin on their lap or tuck a napkin into their clothes to prevent any misplaced food/drink from coming into contact with their clothes thereby causing stains. However, napkins tend to slide off all types of clothing, in particular sheer materials such as silk and therefore do not provide the protection outlined above when needed most for example when wearing an expensive dress at a dinner party.

Applying adhesive to the napkin could mitigate, alleviate or solve one or more these problems.

In this regard, it is known to apply double sided sticky tape to a napkin. However, applying the double sided sticky tape requires a certain degree of human dexterity which may only be copied by a complex machine. Also, waste is produced during the implementation of this solution because the material peeled away from the double sided sticky tape in order to expose the adhesive needs to be disposed of. Furthermore, double sided sticky tape is expensive. These three factors prohibit the implementation of this known solution on a mass scale.

U.S. Pat. No. 4,306,316, DE20306817 and DE202004017373 disclose napkins with adhesive portions that can be adhered to clothing.

WO2011/039533 discloses a napkin. On a first surface of the napkin first and second adhesive portions are adhered so that they are brought into engagement with each other when the sheet is folded in half along a first fold. The adhesive is of a type that will allow the first and second adhesive portions to separate and allow the sheet to be adhered to an object such as clothing.

It is known to provide removable covers or backing strips to protect the adhesive until the protective article, e.g. napkin, is required to be adhered to an object. However, these covers increase the volume required to pack, transport and/or store napkins or the like, which increases the cost of the napkins. For cheap, disposable items such as paper napkins, this extra cost can be a significant fraction of the cost of manufacture.

This extra cost may also discourage consumers from purchasing an adhesive napkin, rather than a cheaper, non-adhesive alternative.

Adhesive napkins would appear to be useful items. However, to date, no commercially successful adhesive napkin has been developed.

It is an object of the invention to address one or more of the shortcomings mentioned herein associated with known protective articles, e.g. napkins, and their manufacture.

SUMMARY OF THE INVENTION

In accordance with a first aspect of the invention there is provided a protective article comprising a sheet with a first surface and at least one adhesive portion arranged on the first surface. The adhesive portion comprises a water-based adhesive that allows the sheet to be non-permanently adhered to an object.

The water-based adhesive may comprise a water-based acrylic adhesive.

The water-based adhesive may comprise an emulsion. In an embodiment, the water-based adhesive may comprise at least 40 parts by weight or at least 50 parts by weight of a water-based acrylic adhesive emulsion. In an embodiment, the water-based adhesive may comprise up to 80 parts by weight or up to 90 parts by weight of a water-based acrylic adhesive emulsion.

A suitable water-based acrylic adhesive may be available in Bostik's Aquagrip® range of adhesives.

The use of a water-based adhesive may provide several advantages, during manufacture and use of the protective article. Advantageously, a water-based adhesive may be relatively safe for users. For instance, a water-based adhesive may not be harmful or irritating to the skin and/or may not be harmful or irritating if it is accidentally licked or eaten by a human or an animal or comes into contact with food which is subsequently eaten.

A water-based adhesive may be relatively safe and easy to handle within the manufacturing environment, e.g. because the water-based adhesive typically will not be flammable. In addition, the water-based adhesive may be applied to the surface of the sheet in ambient air, rather than in a controlled atmosphere, as would be the case with adhesive systems comprising more volatile or harmful solvents. Accordingly, the cost of manufacture may be relatively low.

Conveniently, the water-based adhesive may be particularly well suited to being applied on to the surface of the sheet by spraying. Spraying can be used to apply the adhesive relatively rapidly on to the first surface of the sheet. Accordingly, a production rate of the protective article may be maintained that are comparable with the production rate of similar protective articles not having any adhesive portions.

The or each adhesive portion may be sprayed on to the first surface of the sheet.

As an alternative to spraying, rolling may be used to apply adhesive to the surface of the sheet. Rolling may allow even easier and more rapid application of the adhesive than spraying, particularly when the adhesive is to be applied as a single strip.

Further alternative methods of applying the adhesive to the surface of the sheet include printing and stamping of the adhesive onto the surface of the sheet. These methods may have the advantage of allowing the adhesive to be applied in a pattern.

In contrast, spraying, rolling, printing, and stamping typically cannot be used to apply a hot melt adhesive on to a surface. Further disadvantages of hot melt adhesives include the relative difficulty and risk involved in handling the adhesive and the consequential need for more expensive and complicated manufacturing equipment.

The or each adhesive portion may have any suitable shape, e.g. a polygonal shape or a curvilinear shape having one or more curved sides. For instance, the or each adhesive portion may be triangular, quadrilateral, rectangular, pentagonal, hexagonal, heptagonal, octagonal, elliptical, circular or semicircular. The or each adhesive portion may have the form of an elongate strip. At least a portion of the elongate strip may be straight, zig-zagged, curved or wavy.

A plurality of adhesive portions may be arranged on the first surface.

Colour may be added to the water-based adhesive by the addition of one or more colouring agents, dyes or pigments. Advantageously, the addition of colour may make the adhesive portion(s) more noticeable for users, and/or may allow the adhesive portion(s) to match a colour or pattern on the first surface of the sheet.

The colour of the adhesive portion(s) may be controlled by varying the ratios and amounts of any colouring agents, dyes and/or pigments included in the water-based adhesive.

The ability to add colour to the water-based adhesive is a further advantage of water-based adhesive over other adhesives, in particular hot melt adhesives. Colour cannot readily be added to a hot melt adhesive.

The sheet may be flexible, semi-rigid or rigid. The sheet may be foldable due to being flexible and/or along one or more specific fold lines.

In an embodiment, the sheet may be folded. For instance, the sheet may be folded in half.

The sheet may be folded such that a first portion of the first surface faces a second portion of the first surface.

When the sheet is folded such that a first portion of the first surface faces a second portion of the first surface, a first adhesive portion and a second adhesive portion may be adapted to engage each other. The water-based adhesive is selected such that it is of a type that will allow the first and second adhesive portions to be separated when the sheet is unfolded, in use, and allow the sheet to be adhered to an object.

Alternatively or additionally, when the sheet is folded such that a first portion of the first surface faces a second portion of the first surface, at least one adhesive portion arranged on the first portion of the first surface may be brought into engagement with the second portion of the first surface at a location absent an adhesive portion. The water-based adhesive is selected such that is of a type that will allow the at least one adhesive portion arranged on the first portion of the first surface and the second portion of the first surface to be separated when the sheet is unfolded, in use, and allow the sheet to be adhered to an object.

Embodiments in which, after folding, the or each adhesive portion engages a portion of the first surface of the sheet absent adhesive may advantageously be relatively easier to manufacture, since a lower accuracy in application of the adhesive may be tolerated than when manufacturing an embodiment, in which after folding, two adhesive portions engage each other. Another benefit may be that less force may be required, in use, to unfold an embodiment, in which the or each adhesive portion engages a portion of the first surface of the sheet at a location absent adhesive than to unfold an embodiment in which two adhesive portions engage each other.

In an embodiment, the sheet may comprise a first and a second adhesive portion, the first and second adhesive portions being adapted to engage each other when the sheet is folded, e.g. along a first fold. In an embodiment, the adhesive portion(s) may be arranged symmetrically about a fold line, e.g. the first fold. One or more adhesive portions, e.g. the first and second adhesive portions, may form a strip of adhesive extending a distance along the first surface. In an embodiment, the strip of adhesive may extend substantially perpendicularly to the first fold. The strip of adhesive may be located on an edge or next to an edge of the first surface.

By folding the sheet of material as above, the adhesive portion may be protected until such time as the protective article is required to be used. Thus, removable covers or backing strips may not be required.

However, in some embodiments, one or more adhesive portions may be covered at least partially by a removable cover. The or each removable cover may have a tab portion adapted to be grasped by a user.

The sheet may have been folded prior to application of adhesive.

In an embodiment, the sheet may be folded more than once.

The sheet of material may comprise a second fold. This may be desirable, for example, for packing one or more of the protective articles into a package. The package may be of a standardly sold size for a given protective article.

In an embodiment, one or more adhesive portions may be arranged on a second surface of the sheet.

The sheet may be made from any suitable material, e.g. card, cloth, woven fabric, non-woven fabric, plastic, or single or multiple plies of paper.

The protective article may comprise a protective garment. The protective article may comprise: a napkin, a dental napkin, a napkin for medical use such as a surgical napkin, an apron, a bib, a table cloth, a coaster, a place mat, a furniture cover for indoor or outdoor use or a windscreen cover for a vehicle.

In accordance with a second aspect of the invention, there is provided a method of manufacture of a protective article, the method comprising the steps of:
providing a sheet with a first surface; and
applying at least one adhesive portion on to the first surface;
wherein the or each adhesive portion comprises a water-based adhesive that allows the sheet of material to be non-permanently adhered to an object.

In an embodiment, the adhesive portion(s) may be applied on to the first surface from any direction. For instance, the adhesive portion(s) may be applied on to the first surface from either side of the sheet, e.g. from above or from below.

In an embodiment, applying the at least one adhesive portion on to the first surface may comprise spraying the water-based adhesive. The water-based adhesive may be sprayed from one or more spray heads.

In an alternative embodiment, applying the at least one adhesive portion on to the first surface may comprise rolling the water-based adhesive onto the first surface. In further alternative embodiments, applying the at least one adhesive portion on to the first surface may comprise printing or stamping the water-based adhesive.

The rate of application of the water-based adhesive may be variable. For instance, the rate of application of the water-based adhesive may be varied "on the fly" (i.e. without halting the carrying out of the method) or from one manufacturing run to the next.

The properties of the water-based adhesive, e.g. chemistry, composition and/or colour, may be variable. For instance, the properties of the water-based adhesive may be varied "on the fly" (i.e. without halting the carrying out of the method) or from one manufacturing run to the next.

The water-based adhesive may comprise a water-based acrylic adhesive. The water-based adhesive may comprise one or more colouring agents, dyes and/or pigments.

In an embodiment, the water-based adhesive may be mixed prior to application on to the sheet. Alternatively, two or more components of the water-based adhesive may be applied on to the sheet separately and allowed to mix during and/or after application.

In an embodiment, the method may comprise the step of folding the sheet, e.g. along a first fold, such that either an adhesive portion is brought into engagement with an adhesive-free portion of the first surface, or such that a first adhesive portion is brought into engagement with a second adhesive portion.

The sheet may be initially folded before the application of the adhesive, e.g. such that the first surface comprises the outward face of a folded sheet of material.

In embodiments comprising a first and second adhesive portion, the adhesive portions may be applied, e.g. sprayed, rolled, printed, or stamped, such that the first and second adhesive portions form a strip of adhesive extending a distance along the first surface. For instance, the strip of adhesive may be located on an edge or next to an edge of the first surface.

The method may additionally comprise a step of folding a second fold in the first surface.

The method may comprise the step of drying the at least one adhesive portion. Drying may be accomplished by leaving the sheet to rest in ambient air for a period of time and/or applying heat from a heat source. For instance, the heat source may comprise an infra-red (IR) heat source.

In accordance with a third aspect of the invention there is provided an apparatus for applying adhesive to a sheet comprising: an adhesive applying means operable to spray a water-based adhesive on to a first surface of the sheet, so as to provide at least one adhesive portion on the first surface of the sheet. The water-based adhesive allows, in use, the sheet to be non-permanently adhered to an object.

The water-based adhesive may comprise a water-based acrylic adhesive. The water-based adhesive may comprise one or more colouring agents, dyes and/or pigments.

The adhesive applying means may comprise one or more spray heads.

The adhesive applying means may be operable to vary, e.g. in accordance with a predetermined program or on demand from an operator, the rate of spraying of the water-based adhesive and/or the properties, e.g. chemistry, composition and/or colour, of the water-based adhesive.

In accordance with a fourth aspect of the invention there is provided an apparatus for applying adhesive to a sheet comprising an adhesive applying means operable to roll a water-based adhesive on to a first surface of the sheet, so as to provide at least one adhesive portion on the first surface of the sheet, the water-based adhesive allowing, in use, the sheet to be non-permanently adhered to an object.

The water-based adhesive may comprise a water-based acrylic adhesive. The water-based adhesive may comprise one or more colouring agents, dyes and/or pigments The adhesive applying means may comprise one or more rollers.

In some embodiments, the adhesive may be held in a reservoir before being applied to a roller. Adhesive may be applied to the roller by dipping the roller into the reservoir, or in alternative embodiments adhesive may be pumped from the reservoir and applied to the surface of the roller.

In some embodiments, the apparatus may further comprise an adhesive removing means operable to remove excess adhesive from the roller. Excess adhesive may be removed from the roller before adhesive is rolled onto the first surface. The adhesive removing means may for example be a scraper blade, or another roller.

In accordance with a fifth aspect of the invention there is provided an apparatus for applying adhesive to a sheet comprising: an adhesive applying means operable to print a water-based adhesive on to a first surface of the sheet, so as to provide at least one adhesive portion on the first surface of the sheet, the water-based adhesive allowing, in use, the sheet to be non-permanently adhered to an object.

The water-based adhesive may comprise a water-based acrylic adhesive. The water-based adhesive may comprise one or more colouring agents, dyes and/or pigments In accordance with a sixth aspect of the invention there is provided an apparatus for applying adhesive to a sheet comprising: an adhesive applying means operable to stamp a water-based adhesive on to a first surface of the sheet, so as to provide at least one adhesive portion on the first surface of the sheet, the water-based adhesive allowing, in use, the sheet to be non-permanently adhered to an object.

The water-based adhesive may comprise a water-based acrylic adhesive. The water-based adhesive may comprise one or more colouring agents, dyes and/or pigments In some embodiments of the apparatus according to the fourth, fifth or sixth aspects of the invention, the adhesive applying means may be operable to vary, e.g. in accordance with a predetermined program or on demand from an operator, the rate of application of the water-based adhesive and/or the properties, e.g. chemistry, composition and/or colour, of the water-based adhesive.

The apparatus according to the third, fourth, fifth or sixth aspects of the invention may comprise a delivery means for delivering water-based adhesive to the adhesive applying means.

The apparatus may comprise a storage container for the water-based adhesive. The or a delivery means may be operable to deliver the water-based adhesive from the storage container to the adhesive applying means.

The apparatus may comprise sheet delivery means configured to place the sheet so as to present the first surface of the sheet to the adhesive applying means. The sheet delivery means may be configured to be move, in use, the sheet relative to the adhesive applying means. Alternatively or additionally, the adhesive applying means may be movable relative to the sheet. The first surface of the sheet may be presented to the adhesive applying means in any suitable orientation.

In an embodiment, the apparatus may comprise one or more folding means for folding the sheet along a fold. For instance, the apparatus may comprise one or more folding means configured to fold the sheet along one or more folds after application of the adhesive portion(s). Additionally or alternatively, the apparatus may comprise an initial folding means configured to fold the sheet prior to application of the adhesive portion(s).

In one embodiment of the apparatus, a first folding means may be operable to fold the sheet of material along a first fold such that the at least one adhesive portion is brought into engagement with an adhesive-free portion of the first surface.

In an alternative embodiment of the apparatus, the adhesive applying means may be operable to spray, roll, print, or stamp at least a first and a second adhesive portion onto the first surface; and the or a first folding means may be operable to fold the sheet of material along a first fold such that the first and second adhesive portions are brought into engagement with each other. The adhesive applying means may be operable to apply the first and second portions together to form a strip of adhesive extending a distance along the first surface. The strip of adhesive may be located on an edge of the sheet or adjacent to an edge of the sheet.

The apparatus may further comprise a drying means arranged to dry the adhesive portion(s) on the first surface. The drying means may be located in line with the adhesive applying means. In an embodiment, the drying means may be located downstream of the adhesive applying means and upstream of one or more folding means.

The drying means may comprise any suitable heat source, e.g. an infra-red (IR) heat source such as an IR lamp. The heat source may be controllable to vary the drying rate. In some embodiments, fast drying of the adhesive portion(s) may be desired, in order to maximise the rate of manufacture.

The apparatus may further comprise cutting means for cutting the sheet of material. For example, adhesive may be applied by the apparatus to a large sheet of material, which is subsequently cut to appropriate dimensions for the protective article.

Alternatively, a sheet of material may be cut into sheets of appropriate dimensions prior to application of the adhesive.

In use, a large sheet of material may be continuously fed into the apparatus. The adhesive applying means may be operable continuously or discontinuously, depending on the required arrangement of adhesive portion(s).

The apparatus may comprise an embossing means, a printing means and/or a stamping means for imparting a surface texture or decoration to the sheet.

The apparatus for applying adhesive may be part of an apparatus for manufacturing a protective article. The apparatus for applying adhesive may be retro-fitted to an existing apparatus for manufacturing a protective article.

The apparatus may be configured to produce protective garments such as napkins, dental napkins, aprons, table cloths or furniture covers. The apparatus may comprise a new machine, or may be retrofitted to an existing machine for producing protective garments such as napkins, dental napkins, aprons, table cloths or furniture covers.

A seventh aspect of the invention provides a manufacturing line including an apparatus according to the third aspect of the invention.

A further aspect of the invention provides a protective article comprising:
a sheet having a first surface; and
an adhesive portion arranged on a first portion of the first surface;
wherein the sheet is folded such that the first portion of the first surface faces a second portion of the first surface, thereby bringing the adhesive portion into engagement with an adhesive-free portion of the second portion of the first surface, the adhesive being of a type that will allow the adhesive portion to separate from the second portion of the first surface and allow the sheet to be adhered to an object.

A further aspect of the invention provides a computer-readable medium carrying instructions for the manufacture of a protective article according to the invention. In an embodiment, the instructions may be executable in a three-dimensional (3D) printer.

BRIEF DESCRIPTION OF THE DRAWINGS

The invention is described in further detail below by way of example and with reference to the accompanying drawings, in which.

DESCRIPTION OF THE INVENTION

Figure 1:
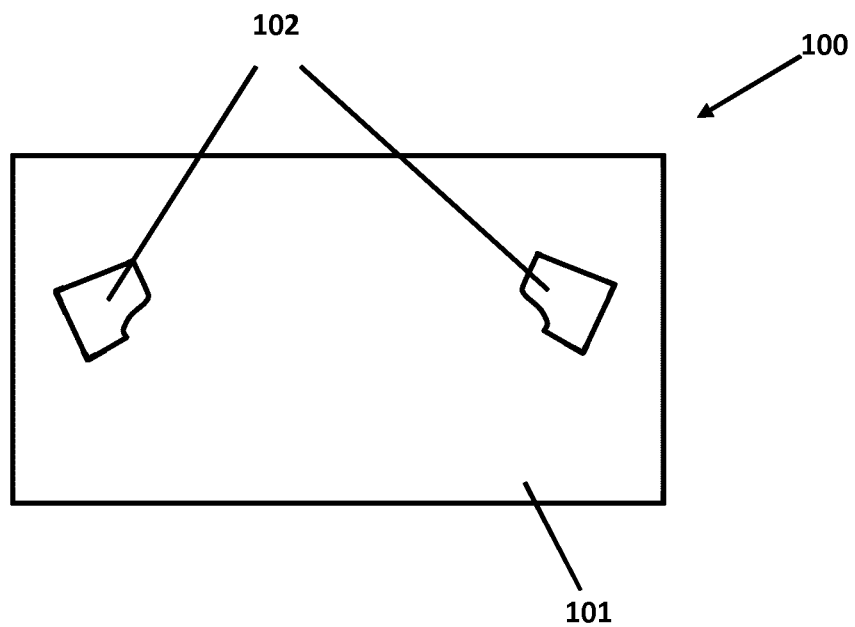
FIG. 1 is a schematic drawing of a protective article according to a first embodiment of the invention.

FIG. 1 illustrates schematically a protective article according to an example embodiment of the invention. The protective article comprises a sheet of material 100. The protective article may be intended for use as a protective garment, such as a napkin, dental napkin, apron, bib, table cloth or furniture cover. The sheet of material 100 may be flexible and/or may be made from any suitable material, including card, cloth, woven fabric, plastic, or single or multiple plies of paper.

The sheet of material 100 has a first surface 101 with two adhesive portions 102 arranged thereon. The adhesive portions comprise a water-based adhesive, which may be a water-based acrylic adhesive.

The adhesive portions 102 may have been produced by spraying, rolling, printing, or stamping the water-based adhesive on to the first surface 101. The water-based adhesive may have been sprayed, rolled, printed, or stamped from above or below the sheet of material 100. The water-based adhesive may have been sprayed at any suitable angle to the first surface 101.

Figure 2:
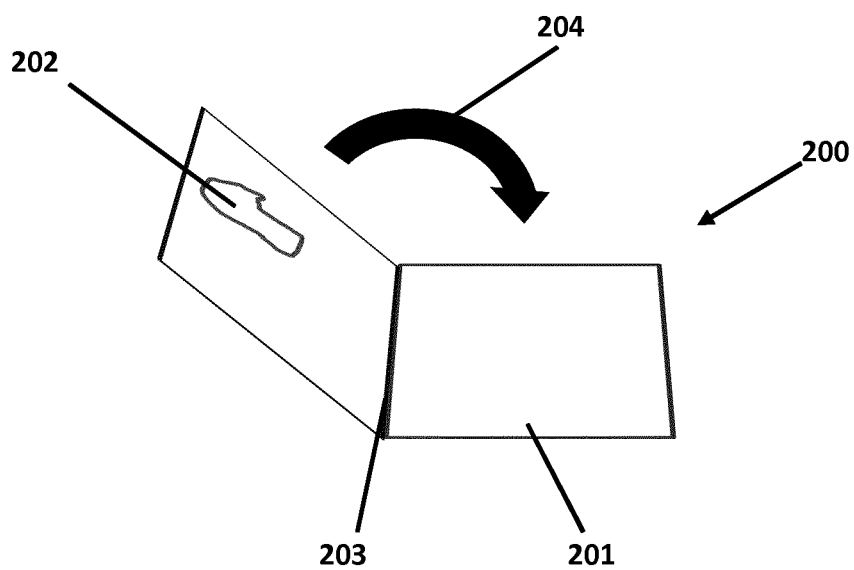
FIG. 2 is a schematic drawing of a protective article according to another example embodiment of the invention.

FIG. 2 illustrates schematically another embodiment of a protective article according to the invention. The protective article comprises a sheet of material 200 comprising a single adhesive portion 202 that has been applied to a first surface 201 of the sheet of material 200. Adhesive portion 202 may be sprayed, rolled, printed or stamped onto the first surface 201. The sheet of material 200 is folded (as indicated by curved arrow 204) along a first fold 203 such that the adhesive portion 202 is brought into engagement with another part of the first surface 201. The adhesive portion 202 may be disengaged from the first surface 201 by unfolding the sheet of material 200.

The embodiment shown in FIG. 2 may be advantageous over other methods of covering the adhesive portion(s). It does not require a cover to be attached to the adhesive portion 202, which would increase the thickness of the folded sheet of material 200. Additionally, as adhesive portion 202 may engage with any part of the first surface 201, less accuracy is required in folding the sheet of material 200, and no restriction is placed on the position or length of the first fold 203. Furthermore, when the sheet of material 200 is in use, for example as a napkin, if adhesive portion 202 is not required, a small piece of the first surface 201 may be folded to engage with it, such that the adhesive portion is covered but the majority of the sheet of material 200 is still available for its intended use, for example preventing food from getting on clothes in the case of a napkin.

Figure 3:
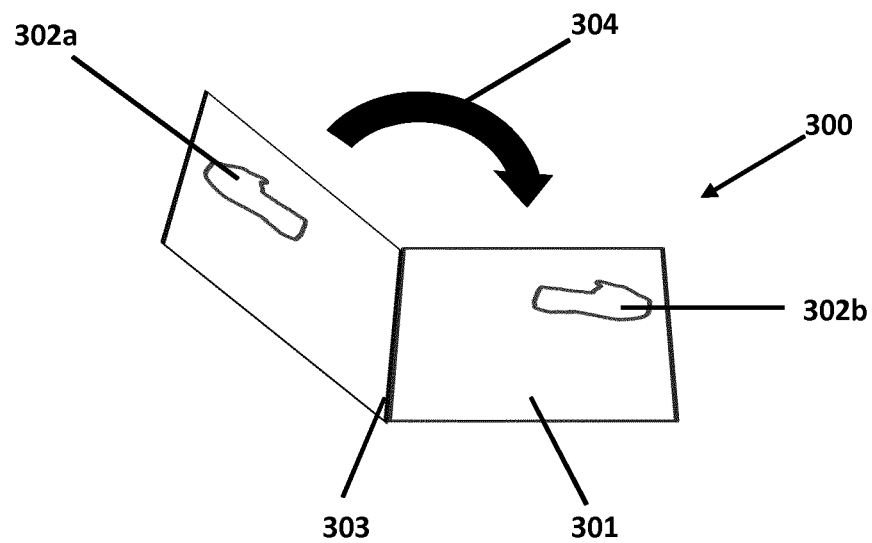
FIG. 3 is a schematic drawing of a protective article according to another example embodiment of the invention.

FIG. 3 illustrates schematically an alternative embodiment of a protective article according to the invention. The protective article comprises a sheet of material 300. In this embodiment, a first portion of adhesive 302a and a second portion of adhesive 302b are applied to a first surface 301 of the sheet of material 300. Adhesive portions 302a and 302b may be sprayed, rolled, printed, or stamped onto the first surface 301. The sheet of material 300 is folded (as indicated by curved arrow 304) along a first fold 303 such that the first adhesive portion 302a and second adhesive portion 302b are brought into engagement with each other. The adhesive portions 302a and 302b may be disengaged by unfolding the sheet of material 300.

In some embodiments, the adhesive strength of two adhesive portions 302a and 302b brought into engagement with each other may be greater than the adhesive strength of one adhesive portion brought into engagement with an adhesive-free portion of the first surface (e.g. as shown in FIG. 2). In some situations, this may be preferable to prevent the sheet of material 300 unfolding until desired. In other situations, such as where the protective article is a napkin for use by the elderly, the embodiment illustrated in FIG. 2 may be preferable, if less force is required to open the napkin. In any event, it will be appreciated that the ease with which the protective article can be unfolded, in use, may be varied and/or controlled by modifying the properties of the adhesive portion(s), e.g. the chemistry, amount and/or concentration of adhesive and/or the size and/or arrangement of the adhesive portion(s).

Figure 4:
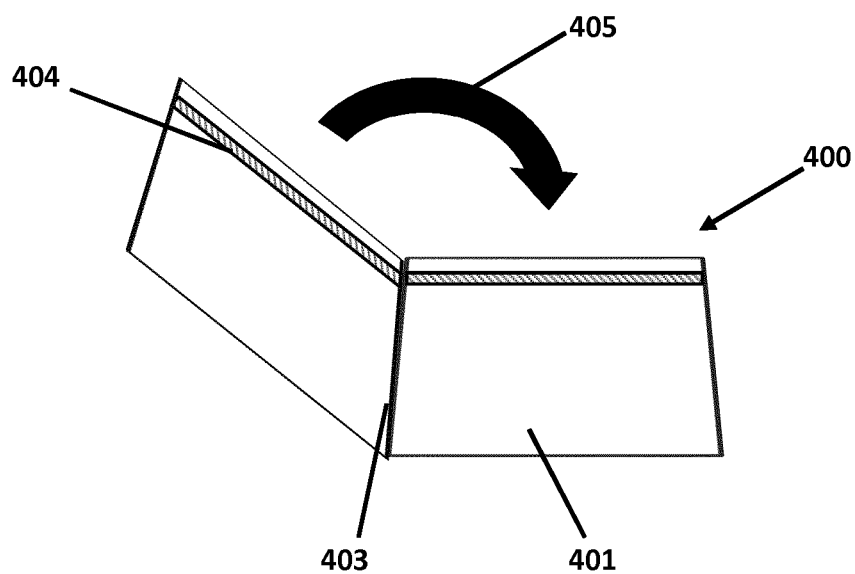
FIG. 4 is a schematic drawing of a protective article according to another example embodiment of the invention.

FIG. 4 illustrates schematically another embodiment of a protective article according to the invention. The protective article comprises a sheet of material 400 with a strip of adhesive 404 extending across a first surface 401 of the sheet of material 400, parallel and relatively close to an edge of the first surface. The strip of adhesive 404 may be located on an edge or next to an edge of the first surface 401. The sheet of material 400 is folded (as indicated by curved arrow 405) along a first fold 403 that is perpendicular to the adhesive strip 404, such that one part of the adhesive strip 404 is brought into engagement with another part of the adhesive strip 404. For example, and as shown in FIG. 4, the first fold 403 may bisect the strip of adhesive 404 such that half of the strip of adhesive 404 covers the other half of the strip of adhesive 404 when the sheet of material 400 is folded.

In some situations, a user of the protective article may temporarily not wish to use the adhesive strip to adhere the sheet of material to an object. By locating a strip of adhesive near an edge of the first surface, the sheet may be folded such that the adhesive strip is covered by the first surface, whilst leaving the majority of the first surface available to cover an object.

Figure 5:
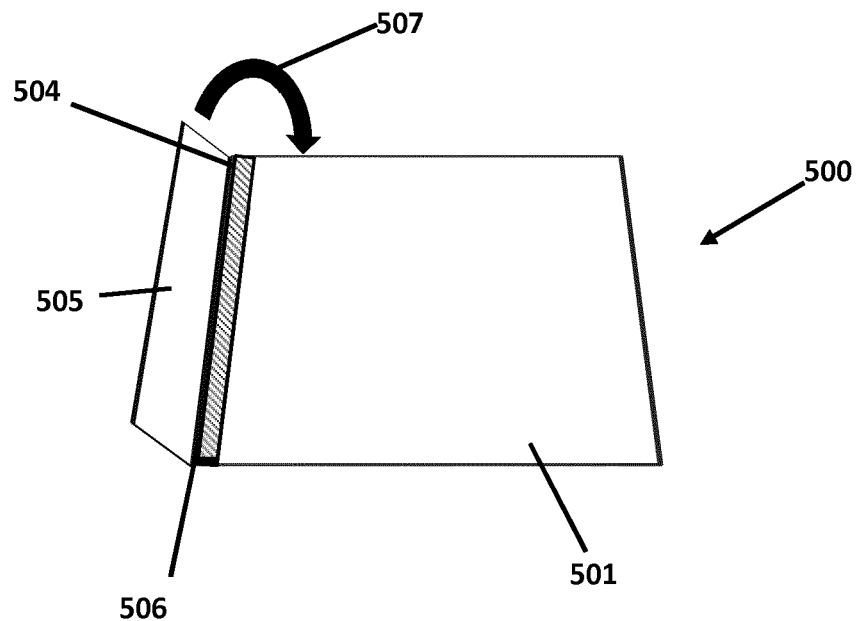
FIG. 5 is a schematic drawing of a protective article according to another example embodiment of the invention.

FIG. 5 illustrates another exemplary embodiment of a protective article according to the invention. The protective article comprises a sheet of material 500 with an adhesive strip 504 applied substantially parallel and close to an edge of a first surface 501 of the sheet of material 500. Adhesive strip 504 may be sprayed, rolled, printed or stamped onto the first surface 501. A portion 505 of the first surface 501 is located between the adhesive strip 504 and the edge of the first surface 501. The portion 505 may be folded (as indicated by curved arrow 507) along a fold 506, such that portion 505 covers adhesive strip 504 without covering the rest of the first surface 501.

During manufacture of the protective article, after a first fold has been made to cover at least partially the adhesive portion(s), at least one further fold, e.g. a second fold, may be made.

Figure 6:
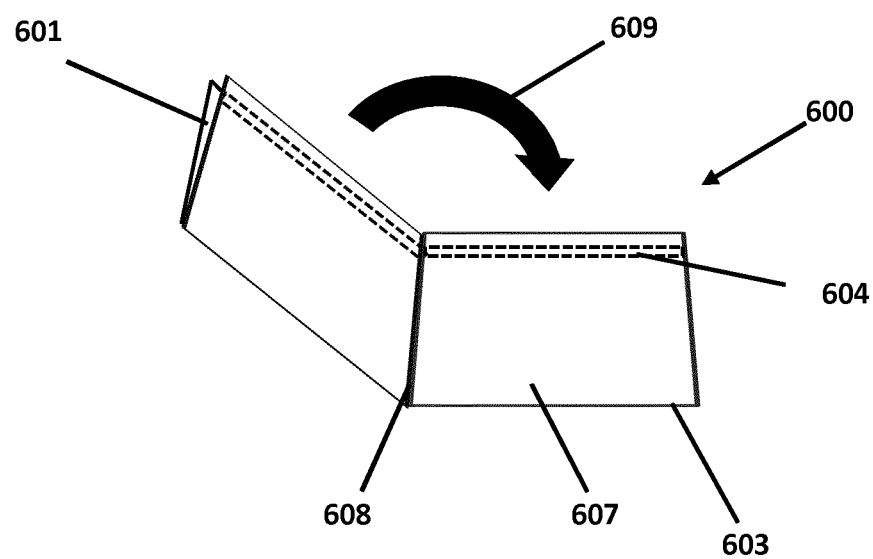
FIG. 6 is a schematic drawing of a protective article according to another example embodiment of the invention.

FIG. 6 illustrates schematically another exemplary embodiment of a protective article according to the invention. The protective article comprises a sheet of material 600, with an adhesive strip 604 sprayed onto a first surface 601 of the sheet of material 600. Adhesive strip 604 may be sprayed, rolled, printed or stamped onto the first surface 601 A second surface 607 comprises the opposing face of sheet of material 600 from the first surface 601.

The sheet of material 600 is folded along a first fold 603 in the manner described in respect of the embodiment illustrated in FIG. 4. The first surface 601 is covered during this fold, so that the second surface 607 is now the outward face of the sheet of material 600.

The sheet of material 600 is subsequently folded (as indicated by curved arrow 609) along a second fold 608 such that one part of the second surface 607 is brought into contact with another part of the second surface 607. In the illustrated example, the second fold 608 is perpendicular to the first fold 603. One or more further folds, e.g. a second fold, may be desirable to reduce the areal dimensions of the sheet of material for packing and transportation.

It should be understood that a second fold may be made in any other embodiment of the protective article, and particularly in the embodiments illustrated in FIGS. 2 and 3.

Alternatively, a fold may be made such that the second surface 607 is brought into contact with itself prior to the application of the adhesive portion 604 on first surface 601.

In embodiments such as this, the first surface on to which the adhesive portion(s) is/are applied comprises the outward face of a folded sheet of material. Optionally, one or more further folds may be made after application of the adhesive portion.

Figure 7:
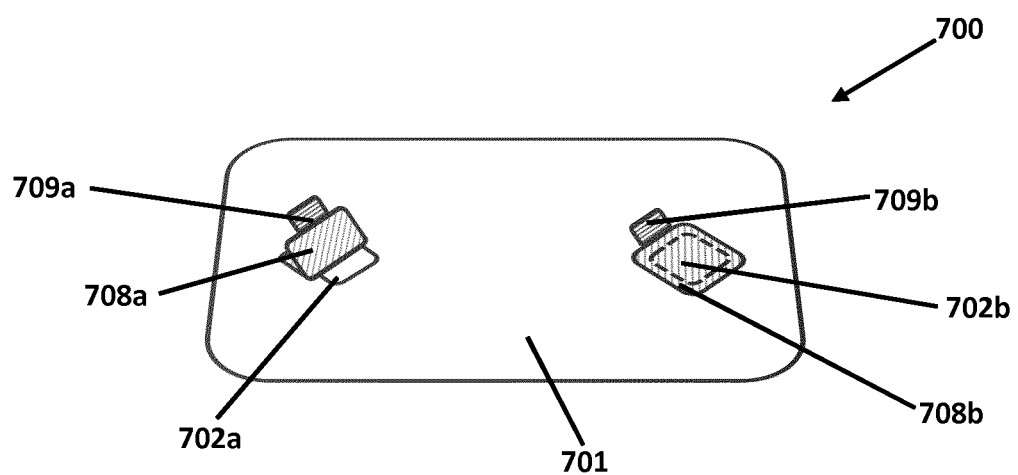
FIG. 7 is a schematic drawing of a protective article according to another example embodiment of the invention.

FIG. 7 illustrates schematically another embodiment of a protective article according to the invention. The protective article comprises a sheet of material 700 with a first surface 701 having two adhesive portions 702a, 702b arranged thereon. Each adhesive portion 702a, 702b is covered by a removable cover 708a, 708b. Each removable cover 708a, 708b has a tab portion 709a, 709b that is adapted to be grasped by a user. By pulling on tab portion 709a, cover 708a can be removed, exposing adhesive portion 702a, which can be used to adhere the sheet of material 700 to an object. Similarly, by pulling on tab portion 709b, cover 708b can be removed, exposing adhesive portion 702b, which can be used to adhere the sheet of material 700 to an object. The removable covers 708a, 708b may be made of any suitable material, such as plastic or metal foil.

Although removable covers may add bulk to the protective article, they may be desirable in some circumstances. For example, they may allow a user to select, in use, only one or some of a plurality of adhesive portions to be exposed.

In the prior art, delays in applying the adhesive have tended to limit the rate at which articles can be manufactured. For instance, some (non-aqueous) solvent-based adhesives may require long drying times, thereby slowing down manufacture. Additionally or alternatively, the use of complicated and/or expensive fume evacuation apparatus may be required when drying such (non-aqueous) solvent-based adhesives, due to release of potentially harmful substances.

Surprisingly, at least some of these problems can be avoided or at least alleviated by using a water-based acrylic adhesive. Such an adhesive typically does not need to be heated in order to be sprayed, rolled, printed, or stamped, reducing energy costs. Furthermore, the adhesive can be rapidly dried, e.g. in ambient air or, if necessary, by using a heat source such as an energy efficient infrared (IR) lamp. No fume evacuation apparatus is required.

By using a water-based adhesive, adhesive protective articles can be manufactured at a rate comparable to the rate of manufacture of non-adhesive protective articles. Hence, the manufacture of protective articles in accordance with the invention may be commercially viable.

Water-based adhesives, e.g. water-based acrylic adhesives, have additional beneficial properties. They are non-flammable, unlike (non-aqueous) solvent-based acrylics, and do not need to be applied in a protective or controlled atmosphere. They can be coloured, unlike hot melt adhesives. Colouring of the adhesive may be desired in order to make the adhesive portion(s) more visible to a user, in order to facilitate positioning of the protective article on the object it is to cover. Alternatively, colouring may be used to match a colour or pattern on the first surface. The water-based adhesive may be coloured by the addition of one or more colouring agents, pigments and/or dyes.

An additional advantage of water-based adhesives, e.g. water-based acrylic adhesives, over hot melt adhesives is that water-based adhesives may lose a relatively large amount of their volume during the drying process. Thus, an adhesive portion formed of water-based adhesive may be thinner and/or lighter than one formed of a hot melt adhesive. This may be beneficial, since, when a sheet of material is folded, for example to form the usual twice-folded squares that napkins are conventionally packaged as, it may be desirable to minimise the additional thickness caused by the adhesive portions. Any additional thickness will reduce the number of sheets of material that can be packaged and transported together. Reducing the thickness of the adhesive portion therefore reduces the cost of transportation of the protective articles. It has been found that applying a water-based acrylic adhesive has a negligible impact on the resulting thickness of the sheet of material, and so does not significantly increase storage and/or transport costs.

Spraying, rolling, printing, or stamping the water-based adhesive on to the first surface forms a film of adhesive on the first surface. After drying, a first side of the film of adhesive is permanently adhered to the first surface. A second, opposing side of the film of adhesive may removably adhere to an object, another part of the first surface, or to another adhesive portion. The second side of the film of adhesive may be disengaged from the object, other part of the first surface or other adhesive portion by applying manual force to separate the adhesive portion from the object, other part of the first surface or other adhesive portion.

When the sheet of material is removed from an object, it should not leave behind any residue. The applicant has found that water-based acrylic adhesives typically do not leave a residue, and so a protective article comprising a sheet with water-based acrylic adhesive portions arranged thereon may be more desirable to a user than other forms of adhesive.

A suitable commercially available water-based acrylic adhesive may be available in the Aquagrip® range from Bostik, Inc.

After the adhesive portion has dried, it may be desirable to cover the adhesive portion, for example to prevent dirt from sticking to the adhesive portion.

In embodiments of the invention, the water-based adhesive is of a type that, when dry, can removably adhere to an object, to an adhesive-free part of the first surface, and/or to another adhesive portion.

Typically, it may be important that applying the water-based adhesive does not slow down the rate at which sheets of material can be produced, and/or does not add significant cost to the manufacture of the protective article. Conveniently, by using a water-based adhesive, the use of spraying, rolling, printing or stamping to apply the water-based adhesive to the surface of the sheet may be facilitated. Spraying, rolling, printing and stamping are examples of a suitably quick and cheap methods of applying adhesive.

An example of a method according to the invention will now be described. Paper is provided on a roll. The roll of paper is unwound and fed continuously to an apparatus, where a surface of the paper is presented towards a sprayhead. The sprayhead is operated to spray water-based acrylic adhesive on to the surface of the paper being fed past the sprayhead. After the adhesive has been sprayed on to the surface of the paper, the paper is fed past an infra-red lamp arranged to dry the adhesive. The paper is then fed through one or more folding means and a cutting means to produce a desired article, e.g. an adhesive paper napkin.

In an alternative example, rolling may be used to apply adhesive to the surface. Rolling may be particularly advantageous for applying adhesive as a strip across the surface. In this example, the surface of the paper is presented towards a roller. Adhesive is applied to the roller either by dipping the roller in a reservoir of adhesive, or by pumping the adhesive from the reservoir onto the roller. Excess adhesive is removed from the roller by a scraper blade, leaving a precise layer of adhesive on the roller. The roller is then be rolled across the surface of the paper to apply the adhesive to the paper, for example in an approximately 3 cm wide strip.

An example of an apparatus according to the invention will now be described. The apparatus may be configured to continuously manufacture a plurality of protective articles such as adhesive paper napkins. The apparatus comprises a means for unwinding paper from a roll and feeding it past a sprayhead such that a surface of the paper is presented towards the sprayhead. The sprayhead is operable to spray water-based acrylic adhesive on to the surface of the paper being fed past the sprayhead. An in-line drying means comprising an infra-red lamp is provided downstream of the sprayhead. In use, the paper is fed past the infra-red lamp arranged to dry the adhesive. Further downstream, the apparatus comprises one or more folding means and a cutting means through which the paper is cut to produce the desired articles, e.g. adhesive paper napkins.

In other embodiments, the adhesive may be applied by rolling, printing or stamping the adhesive onto the surface of the paper. For example, the sprayhead of the above exemplary apparatus may be replaced with a roller for rolling the adhesive, or means for printing or stamping adhesive onto the surface of the paper.

It is important to quickly dry the adhesive portions to prevent any slowing of the rate of manufacture of the protective articles. The drying means of the apparatus is operable to rapidly dry the adhesive portions. The drying means may be an IR source or lamp. IR lamps are highly energy efficient, and so the drying step does not substantially increase the electricity cost of the manufacturing process. Any suitable heat source may be used as a drying means.

In an embodiment, the apparatus may not comprise a drying means, in which case the adhesive portions may be exposed to ambient conditions for a suitable length of time for the adhesive portions to dry.

However, in a high volume, continuous manufacturing process, such as in the manufacture of paper napkins, the provision of an in-line drying means may be preferred, to ensure that production rates can be maintained.

Non-adhesive paper napkins can be manufactured at rates of as much as 350 metres per minute or more. The present invention may allow for comparable production rates to be achieved in the manufacture of adhesive paper napkins.

In some embodiments, the apparatus may comprise cutting means for cutting the sheet of into desired dimensions. Typically, the sheet may be cut after adhesive portions have been applied and all desired folds made in the sheet. This may allow adhesive to be applied continuously. For example, when producing the protective article illustrated in FIG. 4, a continuous strip of adhesive may be applied to a long sheet of material 400, which is subsequently cut into smaller pieces. This may have the advantage of reducing the amount of control and precision required from the adhesive applying means.

Alternatively, a large source of material may be initially cut into sheets of material of desired dimensions, and adhesive portions subsequently may be applied to each sheet of material.

Optionally, the adhesive applying means may be turned off so that the apparatus can be used to produce conventional, non-adhesive protective articles.

Conveniently, the apparatus may be incorporated into an existing device for manufacturing protective articles without adhesive portions. Retrofitting old devices in this way may be more cost effective than purchasing a new apparatus for producing protective articles according to the invention. As described above, use of water-based acrylic adhesives within the retrofitted device may allow the device to run at the same rate, or at least at a comparable rate, as before the addition of the new apparatus.

Advantageously, using a water-based acrylic adhesive allows the adhesive to be sprayed, rolled, printed or stamped directly onto the sheet of material without requiring heating of the adhesive. This can dramatically reduce costs of applying the adhesive. Typically, the water-based acrylic adhesive may be quick to dry, and so can be used in the manufacture of protective articles without slowing down the rate of production.

In some embodiments of the invention, two portions of adhesive are arranged on the sheet in such a way that they come into engagement with one another when the sheet is folded. Consequently, for example, a napkin according to the invention can be subsequently unfolded and adhered to an object such as a person or a person's clothes.

Also, because expensive double sided sticky tape need not be used to realise the present invention, the need to dispose of backing strips may be eliminated. This may provide the advantage of significantly reducing manufacturing costs, from the high cost of using double-sided tape seen in the prior art.

Furthermore, due to the elimination of the requirement for backing strips, less dexterity may be required to apply adhesive to a napkin. The present invention may therefore be implemented quicker using less complicated machinery than that which is already known, thus providing the advantages of further reducing the cost of, and increasing the speed at which, protective articles according to the invention can be manufactured.

One of the most significant cost factors in the production of napkins is transportation. This results from the very light-weight nature of this product making it inefficient to transport in that the vehicle carrying the product is capable of carrying significantly heavier goods within its volume. It is therefore important in the transportation of napkins that the packaged product is transported in as compacted and compressed form as possible. The use of double-sided tape (or any other reinforcing tape) will increase the bulk of the napkins within their packaging meaning that fewer napkins can be transported per unit of volume. The volume of and weight of the napkins of the present invention is barely distinguishable from that of a plain napkin without adhesive and therefore can be treated exactly like a non-adhesive napkin of the prior art. Indeed once the adhesive has been applied and subsequently folded so that the adhesive has been covered, the napkin can then be handled in exactly the same manner as a non-adhesive napkin.

It is also the case that heavy woven (non-disposable) napkins are often used to reduce the likelihood of them being dislodged since the heavier fabric is less likely to be blown off the lap of the person wearing it. Although the present invention is equally applicable to heavy fabric napkins, further reducing the likelihood of slippage, the present invention means that there may be less need to use such heavy material which may reduce the cost of laundry and/or make disposable napkins a more environmentally sustainable alternative. Furthermore, the same or similar advantages may be realised, for example, when applying the invention to table cloths, coasters and place mats.

Furthermore, the present invention may be of particular use for people of limited mobility or in places where mobility is limited. For example, the elderly, people with certain movement limiting disabilities and children may easily lose their napkin and not be able to retrieve it. Similarly in cramped conditions, such as on an aeroplane it may not be easy to reach a dropped napkin. For people who are partially sighted, and for the fully sighted in low light conditions, it is easy to not realise that a napkin is no longer in position. Because the present invention ensures the napkin remains in place this problem is alleviated.

It is envisaged that the present invention could enable a step-change in the popularity and commercial uptake of adhesive napkins or other protective articles. In particular, the present invention may alleviate one or more of the obstacles to cost-effective manufacture of adhesive napkins or other protective articles.

Protective articles according to the invention may be used in many applications and environments. For instance, protective articles according to the invention may be used to protect a person's clothing in the case of a napkin, dental napkin, or napkin for medical use. Alternatively, objects such as furniture or parts thereof, e.g. tables, sideboards, work surfaces and the like, may be protected using a protective article according to the invention.

Napkins and other tableware, e.g. coasters, table cloths, place mats, according to the invention may be particularly useful in the catering and hospitality industries, e.g. for events, in hotels and restaurants, in hospitals and on board aeroplanes, buses, trains or boats such as cruise ships.

While the invention has been disclosed with reference to certain exemplary embodiments, many modifications may be apparent to the person skilled in the art without departing from the scope of the invention.

The invention claimed is:

1. A protective article comprising a sheet with a first surface and a first adhesive portion and a second adhesive portion arranged on the first surface, wherein each adhesive portion comprises a water-based acrylic adhesive that allows the sheet to be non-permanently adhered to an object, wherein the sheet is foldable, and wherein, when the sheet is folded such that a first portion of the first surface faces a second portion of the first surface, the first adhesive portion and the second adhesive portion engage each other, the water-based acrylic adhesive being selected such that it is of a type that will allow the first and second adhesive portions to be separated when the sheet is unfolded, in use, and allows the sheet to be adhered to an object, wherein none of the adhesive portions is/are covered by a removable cover or backing strip.

2. The protective article according to claim 1, wherein the water-based acrylic adhesive comprises at least 40 parts by weight of a water-based acrylic emulsion and/or up to 90 parts by weight of a water-based acrylic emulsion.

3. The protective article according to claim 1, wherein the at least one adhesive portion has a polygonal shape or a curvilinear shape having one or more curved sides.

4. The protective article according to claim 1, wherein the at least one adhesive portion has the form of an elongate strip.

5. The protective article according to claim 1, wherein the water-based adhesive is coloured by the addition of one or more colouring agents, dyes and/or pigments.

6. The protective article according to claim 1, wherein the sheet is folded more than once.

7. The protective article according to claim 1, wherein one or more adhesive portions are arranged on a second surface of the sheet.

8. The protective article according to claim 1, wherein the sheet is made from card, cloth, woven fabric, non-woven fabric, plastic, or single or multiple plies of paper.

9. The protective article according to claim 1, wherein the protective article comprises a napkin, a dental napkin, a napkin for medical use, a surgical napkin, an apron, a bib, a table cloth, a coaster, a place mat, a furniture cover for indoor or outdoor use or a windscreen cover for a vehicle.

10. The protective article according to claim 1, wherein the at least one adhesive portion is sprayed, printed or stamped on to the first surface of the sheet.

11. A protective article comprising a sheet with a first surface and an adhesive portion arranged on the first surface, wherein the sheet is made from card, cloth, woven fabric, non-woven fabric, plastic, or single or multiple plies of paper, wherein the adhesive portion comprises a water-based acrylic adhesive that allows the sheet to be non-permanently adhered to an object, wherein the sheet is foldable, and wherein, when the sheet is folded such that a first portion of the first surface faces a second portion of the first surface, the adhesive portion arranged on the first portion of the first surface is brought into engagement with the second portion of the first surface at a location comprising only the card, cloth, woven fabric, non-woven fabric, plastic, or single or multiple plies of paper from which the sheet is made and absent the adhesive portion, the water-based adhesive being selected such that it is of a type that will allow the adhesive portion arranged on the first portion of the first surface and the second portion of the first surface to be separated when the sheet is unfolded, in use, and allows the sheet to be adhered to an object, wherein none of the adhesive portion is covered by a removable cover or backing strip.

12. The protective article according to claim 11, wherein the water-based acrylic adhesive comprises at least 40 parts by weight of a water-based acrylic emulsion and/or up to 90 parts by weight of a water-based acrylic emulsion.

13. The protective article according to claim 11, wherein the at least one adhesive portion has a polygonal shape or a curvilinear shape having one or more curved sides.

14. The protective article according to claim 11, wherein the at least one adhesive portion has the form of an elongated strip.

15. The protective article according to claim 11, wherein the water-based adhesive is coloured by the addition of one or more colouring agents, dyes and/or pigments.

16. The protective article according to claim 11, wherein the sheet is folded more than once.

17. The protective article according to claim 11, wherein one or more adhesive portions are arranged on a second surface of the sheet.

18. The protective article according to claim 11, wherein the protective article comprises a napkin, a dental napkin, a napkin for medical use, a surgical napkin, an apron, a bib, a table cloth, a coaster, a place mat, a furniture cover for indoor or outdoor use, or a windscreen cover for a vehicle.

19. The protective article according to claim 11, wherein the at least one adhesive portion is sprayed, printed or stamped on to the first surface of the sheet.

* * * * *

UNITED STATES PATENT AND TRADEMARK OFFICE
CERTIFICATE OF CORRECTION

Page 1 of 1

PATENT NO. : 10,759,143 B2
APPLICATION NO. : 15/537982
DATED : September 1, 2020
INVENTOR(S) : Gail Shaw It is certified that error appears in the above-identified patent and that said Letters Patent is hereby corrected as shown below:

In the Claims

Column 15, Line 30, Claim 1, after "portions" delete "is/arc"

Signed and Sealed this
Eighth Day of March, 2022

Drew Hirshfeld
*Performing the Functions and Duties of the*
*Under Secretary of Commerce for Intellectual Property and*
*Director of the United States Patent and Trademark Office*